US010603287B2

(12) United States Patent
Yen (10) Patent No.: US 10,603,287 B2
(45) Date of Patent: Mar. 31, 2020

(54) ALBUMIN NANOSPHERE PREPARATIONS TO CONTROL BLEEDING FROM SURGICAL OPERATIONS (71) Applicant: Richard C. K. Yen, Yorba Linda, CA (US)

(72) Inventor: Richard C. K. Yen, Yorba Linda, CA (US)

(73) Assignee: PTLNV, LLC, Series Three (3), Las Vegas, NV (US)

(*) Notice: Subject to any disclaimer, the term of this patent is extended or adjusted under 35 U.S.C. 154(b) by 11 days.

(21) Appl. No.: 15/618,234

(22) Filed: Jun. 9, 2017

(65) Prior Publication Data
US 2018/0021264 A1    Jan. 25, 2018

Related U.S. Application Data (60) Provisional application No. 62/364,764, filed on Jul. 20, 2016.

(51) Int. Cl.
| *A61K 9/50* | (2006.01) |
| *A61K 9/10* | (2006.01) |
| *A61K 9/08* | (2006.01) |
| *A61K 9/16* | (2006.01) |
| *A61K 47/10* | (2017.01) |
| *A61K 38/38* | (2006.01) |

(52) U.S. Cl.
CPC .............. *A61K 9/50* (2013.01); *A61K 9/08* (2013.01); *A61K 9/10* (2013.01); *A61K 9/1676* (2013.01); *A61K 38/38* (2013.01); *A61K 47/10* (2013.01)

(58) Field of Classification Search
CPC . A61K 9/50; A61K 9/10; A61K 47/10; A61K 38/38; A61K 9/08; A61K 9/1676
See application file for complete search history.

(56) References Cited

U.S. PATENT DOCUMENTS

| 4,440,679 | A | 4/1984 | Fernandes et al. | |
| 6,221,668 | B1 | 4/2001 | Ryan et al. | |
| 6,262,019 | B1 | 7/2001 | Keller et al. | |
| 6,264,988 | B1* | 7/2001 | Yen | A61K 9/1676 424/489 |
| 6,916,795 | B1 | 7/2005 | Youssef | |
| 7,625,878 | B2 | 12/2009 | Stella et al. | |
| 9,114,127 | B2 | 8/2015 | Yen | |
| 9,226,898 | B1 | 1/2016 | Yen | |
| 9,351,925 | B2 | 5/2016 | Yen | |
| 9,629,931 | B2 | 4/2017 | Yen | |
| 2002/0142046 | A1* | 10/2002 | Yen | A61K 9/1611 424/491 |
| 2011/0189299 | A1 | 8/2011 | Okubo et al. | |
| 2014/0030347 | A1 | 1/2014 | Yen | |
| 2014/0212358 | A1* | 7/2014 | Yen | A61K 49/0008 424/9.2 |
| 2016/0045573 | A1 | 2/2016 | Yen | |
| 2016/0082086 | A1 | 3/2016 | Yen | |
| 2016/0354481 | A1 | 12/2016 | Yen | |

FOREIGN PATENT DOCUMENTS

WO    2013036902 A1    3/2013

OTHER PUBLICATIONS

Elzoghby et al, Journal of Controlled Release, 157, 168-182 (Year: 2012).*
Muller et al, Pharmaceutical Research, vol. 13, No. 1, 32-37 (Year: 1996).*
Elzoghby et al, Journal of Controlled Release, 2012, 157, 168-182 (Year: 2012).*
Muller et al, Pharmaceutical Research, vol. 13, No. 1, 32-37,1996 (Year: 1996).*
European Commission, "Commission Implementing Decision (Dec. 2, 2015)", EU orphan designation No. EU/3/15/1442, Feb. 12, 2015.
European Medicines Agency, "Public summary of opinion on orphan designation", EMA/COMP/55779/2015, Committee for Orphan Medicinal Products, Mar. 30, 2015.
World Health Organization, "Guidelines on viral inactivation and removal procedures intended to assure the viral safety of human blood plasma products", Annex 4, WHO Technical Report, Series No. 924, 2004.
Hosseini et al., "Study of the Heat-Treated Human Albumin Stabilization by Caprylate and Acetyltryptophanate", Dept. of R&D, Blood Research and Fractionation Co., Tehran, Iran, Iranian Biomedical Journal 6 (4): /35-140 (Oct. 2002).
Dr. Anrei Gudkov, Radiation Sickness Cures and Anti-Radiation Pills, http://nextbigfuture.com/2009/07/radiation-sickness-cures-and-anti.html, Jul. 20, 2009.
Smiley et al., "Fibrinogen stimulates macrophate chemokine secretion through toll-like receptor 4" J Immunol. Sep. 1, 2001; 167(5) abstract.
Perdomo et al., "Quinine-induced thrombocytopenia: drug-dependent GPIb/IX antibodies inhibit megakaryocyte and proplatelet production in vitro". Blood Jun. 2, 2011 vol. 117 No. 225975-5986.
Reiter et al., "Vitamin E and excessive bleeding" Ugeskr Laeger, Dec. 5, 2005; 167(49) (abstract).
Manjunatha, Antiboagulant proteins from snake venoms:structure, function and mechanism. Biochem J. (2006) 397, 377-387.
Blajchman,1996, "Evaluation of the in vivo Hemostatic Function of Human Platelets and Platelet Substitutes in a Thrombocytopenic Rabbit Model", In "Frozen Platelets and Platelet Substitutes in Transfusion Medicine" Mar. 7, 1996.

(Continued)

Primary Examiner — Sudhakar Katakam
(74) Attorney, Agent, or Firm — David Guerra (57) ABSTRACT

The present invention relates to a product, method of making and method of using an albumin sphere suspension for controlling bleeding of a non-thrombocytopenic patient before, during and after surgery. An albumin sphere suspension containing submicron albumin spheres is prepared, with the albumin spheres being capable of controlling bleeding in vivo. The suspension is prepared by mixing at near freezing temperatures an albumin solution, a sub-stabilizing concentration of glutaraldehyde solution and an alcohol solution containing a stabilizing concentration of glutaraldehyde. The mixed suspension is warmed, and glycine and sorbitol being added. Lyophilization of the suspension can be performed for stabilization of the suspension.

20 Claims, 1 Drawing Sheet

(56) References Cited

OTHER PUBLICATIONS

CDC, 2013, "Acute Radiation Syndrome Fact Sheet for Physicians", http://www.bt.cdc.gov/radiation/arsphysicianfactsheet.asp, Page last reviewed: Oct. 22, 2013, Page last updated: Aug. 21, 2014.
CDC, 2014, "Questions and Answers on Ebola", CDC: Page last reviewed: Oct. 24, 2014, Page last updated: Oct. 24, 2014.
CDC, 2014, "Signs and Symptoms of Ebola", CDC: Page last reviewed: Oct. 18, 2014, Page last updated: Oct. 18, 2014.
Chen, 2014, "Edaravone Protects Human Peripheral Blood Lymphocytes from Gamma Irradiation-induced Apoptosis and DNA Damage", Cell Stress Chaperones, Sep. 3, 2014.
Gaugler, 2005, "A Unifying System: Does the Vascular Endothelium Have a Role to Play in Multi-organ Failure Following Radiation Exposure?", BJR Suppl. 2005;27:100-5.
Higgins, 2014, "Ebola Facts: How Many Ebola Cases are Outside of West Africa?", by Andrew Higgins Oct. 17, 2014, New York Times.
Hutchinson, 2007, "Cytokine and Chemokine Expression in Humans Infected with Sudan Ebola Virus", Reprints or correspondence: Dr. Karen L. Hutchinson, Special Pathogens Branch, MS G-14, Centers for Disease Control and Prevention, 1600 Clifton Rd. NE, Atlanta, GA 30333 (kbh6@cdc.gov).
Kalamida, 2014, "Important Role of Autophagy in Endothelial Cell Response to Ionizing Radiation", PLoS One 9(7): e102408. doi:10.1371/journal.pone.0102408.
Kelland, 2014, "More Cases of Ebola in Europe 'Unavoidable', WHO says", Reuters.com, Kate's Feed EMEA Health and Science Correspondent, Oct. 8, 2014.
King, 2014, "Ebola Virus Infection", http://emedicine.medscape.com/article/216288-overview.
Li, 2006, "The Preclinical and Clinical Trial of Platelet Substitute—Fibrinoplate", 4th Asian Pacific Congress on Thrombosis and Haemostasis, Suzhou, China, Sep. 23, 2006.
Rithidech, 2012, "Attenuation of Oxidative Damage and Inflammatory Responses by Apigenin Given to Mice After Irradiation", Mutat Res. Dec. 12, 2012;749(1-2):29-38. doi: 10.1016/j.mrgentox.2012.08.001. Epub Aug. 15, 2012.
Sanchez, 2004, "Analysis of Human Peripheral Blood Samples from Fatal and Nonfatal Cases of Ebola (Sudan) Hemorrhagic Fever: Cellular Responses, Virus Load, and Nitric Oxide Levels", J. Virol. Oct. 2004 vol. 78No. 19 10370-10377.
Sullican, 2003, "Ebola Virus Pathogenesis: Implications for Vaccines and Therapies", doi: 10.1128/JVI.77.18.9733-9737.2003, J. Virol. Sep. 2003 vol. 77 No. 18 9733-9737.
Sung, 2014, "Fibrinogen Coasted Nanospheres Prevent Thrombocytopenia-related Bleeding", American Society of Hematologists annual meeting, Dec. 2014.
Winslow, 2013, "Oxygen: the Poison is in the Dose, Transfusion", Feb. 2013;53(2):424-37, doi: 10.1111/i.1537-2995.2012.03774.x. Epub Jul. 15, 2012.
Yang, 1998, "Distinct Cellular Interactions of Secreted and Transmembrane Ebola Virus Glycoproteins", Science Feb. 13, 1998:279 (5353):1034-7.
Yen, 1995, "A Novel Approach to Correcting the Bleeding Associated with Thrombocytopenia", Presented to American Association of Blood Banks: 48th annual meeting, Nov. 11-15, 1995.
Kutler et al., Annu Rev Med; 2009, 60:193-206.
Yasukochi et al., "Radiation-induced skin ulcer and rib fractures following percutaneous coronary internetion (PCI): A case of right back skin ulcer and adjacent rib fracture after single PCI", J. Dermatol,Mar. 20, 2015, doi: 10.1111/1346-8138.12839.
Shope et al., "Radiation-induced Skin Injuries from Fluoroscopy", RadioGraphy 1996, 16:1195-1199.
Xiao We Mao et al., "Effects of Fibrinoplate-S in a Radiated Mice Model", an abstract at the Radiation Research Society Annual Meeting held in Weston, FL, Sep. 19-22, 2015.
Nauth et al., "Stem Cells for the Repair and Regeneration of Bone" published in Indian J Orthop. Jan.-Feb. 2012; 46(1): 19-21.

* cited by examiner

ALBUMIN NANOSPHERE PREPARATIONS TO CONTROL BLEEDING FROM SURGICAL OPERATIONS

CROSS-REFERENCE TO RELATED APPLICATION

The present application claims priority under 35 U.S.C. 119(e) based upon U.S. Provisional Application No. 62/364,764 filed Jul. 20, 2016. The entire disclosure of the prior application is incorporated herein by reference.

BACKGROUND OF THE INVENTION

Field of the Invention

The present invention relates to albumin nanosphere preparations and method for use in connection with controlling of bleeding before, during and after a surgical operation.

Description of the Prior Art

Bleeding before, during and after a surgical operation is a serious matter.

Some patients start to bleed before the operation. If the bleeding site is external and obvious, pressure can be applied to temporarily stop the bleeding. If the red cell concentration (or hemoglobin concentration) is too low, blood transfusion (typically packed red blood cells) will be administered so that the patient can tolerate the anesthesia as well as further blood loss during the surgery.

Due to the nature of surgical interventions, there will be some blood loss from the surgical cut. The surgeon will try to minimize blood loss by not cutting blood vessels directly if possible. Even so, in many tissues, the blood will "ooze" out anyway from damaged tissues without the surgeon having to make a surgical cut across the tissue. In those cases, the surgeon will use "cotton swabs" or absorbent material to soak up the blood, so that he can at least have a clear view of the surgical site to continue and finish the surgery. However, any such bleeding due to the physical condition of the patient, the difficulty of the surgical site, or due to the cut from the surgical knife, will require the surgical team to spend time clearing the surgical field, which will prolong the surgical time. Long surgical time can be expensive due to the large number of other highly paid personnel around to help with anesthesia and the surgery.

Some surgeries will have continued blood loss postoperatively even though the surgeon controls bleeding adequately during the operation. Examples include the operation of the knee or hip: blood will continue to be lost from the matrix of the bone, which the surgeon cannot "close with a suture." When it is found that the patient has become thrombocytopenic, platelets will be transfused. If the coagulation system is dysfunctional, coagulation factors (or a combination of coagulation factors, such as found in fresh frozen plasma, or cryoprecipitate) will be transfused. Unfortunately, transfusion of blood products often leads to transfusion reactions which can cause additional complications for the patient.

Therefore, it is beneficial to have a product that can control bleeding before, during and after a surgical operation so that the health provider spends less time clearing the surgical site and can complete the surgery faster. The patient will benefit from reduced morbidity, a faster discharge from the hospital and suffering less from complications of transfusions.

The manufacture of albumin spheres, with or without the addition of coagulation factors, particularly of fibrinogen, during the manufacturing of the spheres, are in the public domain, such as U.S. Pat. No. 6,264,988 issued on Jul. 24, 2001 to Yen entitle "Albumin nanosphere preparations and method". The Yen reference disclosed the properties of many albumin microspheres and their application in disease states. However, most of the applications are for thrombocytopenic subjects.

The present invention comprises of a new method of making massive quantities of albumin nanospheres with high yield and with greater uniformity (narrower distribution of size within the population of spheres) of size. The method overcomes one of the most difficult challenges disclosed in Yen's prior art references. In addition, the present invention is a product, a suspension useful in many medical application, including the control of bleeding in a surgical setting, particularly for surgeries on soft tissues which have great tendency to bleed intraoperatively because there is no way for a surgeon to tie a suture around the cut surface. One example of such an organ is the liver.

While the above-described devices fulfill their respective, particular objectives and requirements, the aforementioned patents do not describe albumin nanosphere preparations and method that allows controlling of bleeding before, during and after a surgical operation. The above-identified patents make no provision for use in the controlling of bleeding before, during and after a surgical operation Therefore, a need exists for a new and novel albumin nanosphere preparations and method that can be used for controlling of bleeding before, during and after a surgical operation. In this regard, the present invention substantially fulfills this need. In this respect, the albumin nanosphere preparations and method according to the present invention substantially departs from the conventional concepts and designs of the prior art, and in doing so provides an apparatus primarily developed for the purpose of controlling of bleeding before, during and after a surgical operation.

BRIEF SUMMARY OF THE INVENTION

In view of the foregoing disadvantages inherent in the known types of albumin nanosphere preparations and method now present in the prior art, the present invention provides a novel albumin nanosphere preparations and method, and overcomes the above-mentioned disadvantages and drawbacks of the prior art. As such, the general purpose of the present invention, which will be described subsequently in greater detail, is to provide a new and novel albumin nanosphere preparations and method and method which has all the advantages of the prior art mentioned heretofore and many novel features that result in a albumin nanosphere preparations and method which is not anticipated, rendered obvious, suggested, or even implied by the prior art, either alone or in any combination thereof.

To attain this, the present invention essentially includes an albumin nanosphere preparation, a method of making an albumin sphere suspension and a method of using an albumin sphere suspension for controlling bleeding of a non-thrombocytopenic patient before, during and after surgery.

The present invention includes an albumin nanosphere preparation for administration to a patient to control of bleeding before, during and after surgery. The albumin nanosphere preparation can include a suspension of albumin spheres formed initially by equilibrium between albumin molecules and alcohol molecules without the formation of stable crosslinkage between neighboring albumin molecules at a temperature between 2° C. and 6° C. The suspension of albumin spheres is then subjected by a period of effective crosslinkage at a temperature between 18° C. and 25° C. resulting in the suspension of the of albumin spheres that are stabilized with a distribution of size.

The present invention further includes a method of producing a suspension of albumin spheres for administration to a patient to control of bleeding before, during and after surgery. The method can include:

(a) cooling an albumin solution, a sub-stabilizing concentration of glutaraldehyde solution and an alcohol solution containing a stabilizing concentration of glutaraldehyde to a temperature between 2° C. and 6° C.;

(b) mixing the albumin solution, the sub-stabilizing concentration of glutaraldehyde solution and the alcohol solution at a temperature between 2° C. and 6° C. to produce spheres in a suspension which are not stabilized against resolubilization;

(c) maintaining the temperature of the suspension including the spheres between or at 2° C. and 6° C.; and (d) warming the suspension including the spheres to a temperature between 18° C. and 25° C.

The method may also include adding of a fibrinogen containing solution to the suspension after the step of warming the suspension to coat the spheres with fibrinogen molecules after the spheres had been stabilized against resolubilization.

Still further, the method may include the addition of glycine and sorbitol, with lyophilization of the suspension.

Even further, the method may include an additional step of lyophilization of the suspension which may include:

freezing the suspension at a first temperature for a first time period;

reheating the suspension at a second temperature for a second time period;

adding additional sorbitol and glycine to the suspension;

freezing the suspension at a third temperature for a third time period; and reheating the suspension at a fourth temperature for a fourth time period.

Even still further, the present invention may include a method of using a suspension of albumin spheres for administration to a non-thrombocytopenic patient to control of bleeding before, during and after surgery.

There has thus been outlined, rather broadly, features of the invention in order that the detailed description thereof that follows may be better understood and in order that the present contribution to the art may be better appreciated.

There are, of course, additional features of the invention that will be described hereinafter and which will form the subject matter of the claims attached.

Numerous objects, features and advantages of the present invention will be readily apparent to those of ordinary skill in the art upon a reading of the following detailed description of the present invention, but nonetheless illustrative, embodiments of the present invention when taken in conjunction with the accompanying drawings.

It is therefore an object of the present invention to provide a new and novel albumin nanosphere preparations and method that has all of the advantages of the prior art fibrinogen-coated microspheres and none of the disadvantages.

It is another object of the present invention to provide a new and novel albumin nanosphere preparations and method that may be easily and efficiently manufactured and marketed.

An even further object of the present invention is to provide a new and novel albumin nanosphere preparations and method that has a low cost of manufacture with regard to both materials and labor, and which accordingly is then susceptible of low prices of sale to the consuming public, thereby making such albumin nanosphere preparations and method economically available to the buying public.

Still another object of the present invention is to provide a new albumin nanosphere preparations and method that provides in the apparatuses and methods of the prior art some of the advantages thereof, while simultaneously overcoming some of the disadvantages normally associated therewith.

Even still another object of the present invention is to provide albumin nanosphere preparations and method for controlling of bleeding before, during and after a surgical operation. This allows for a reduction in blood loss and a reduction in surgery time.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

The present invention deals in particular with preparations that have been lyophilized and have long shelf-lives, possibly more than 10 years of stability during storage in room temperature that can be reconstituted with water or saline, for subsequent infusion into patients to control bleeding before, during or after surgery.

The present invention comprises of a new method of making massive quantities of albumin nanospheres with high yield and with greater uniformity (narrower distribution of size within the population of spheres) of size. The method overcomes one of the most difficult challenges disclosed in the prior art. In addition, the present invention is a product, a suspension useful in many medical application, including the control of bleeding in a surgical setting, particularly for surgeries on soft tissues which have great tendency to bleed intraoperatively because there is no way for a surgeon to tie a suture around the cut surface. One example of such an organ is the liver.

The liver has two major sources of blood supply. The hepatic artery brings in oxygenated blood but it supplies only about 20% of the blood going to the liver. The other supply (about 80%) comes from the hepatic portal vein, which carries nutrient-laden blood from the intestine. In patients suffering from cancer of the liver, the liver itself is already distorted by the cancer. The need to dissect the various healthy tissues away from the cancer will also take much attention and effort from the surgeon. Special techniques have to be used to reduce blood flow to the liver; otherwise the patient will die from bleeding on the operation table. Yet, reducing blood flow from the hepatic artery to the liver may deprive the liver of the needed oxygen, thus condemning the patient to death from liver failure after the surgery. The other approach is to restrict the blood flow from the hepatic portal vein; but that will cause a back-up of the blood leading to congestion of the intestine, causing other problems. Therefore, it will greatly benefit the patient as well as the surgical staff if a product such as the present invention can be administered to reduce the amount of spontaneous bleeding without compromising oxygen supply to the liver or causing congestion of blood vessels in near-by and related organs.

It has been the practice with many surgeons nowadays to perform "living donor hepatectomy" which means removing a large portion of a healthy donor's liver (typically the right lobe) and then transplanting the portion to a patient who can benefit from the transplant. However, the transplanted liver lobe has to be large enough to sustain the need of the transplanted patient. Therefore the living donor takes the risk of having major blood loss during and after the surgery.

Patients who have liver cancer are difficult to treat because they often have liver dysfunction or failure even before the surgery. The liver is the major organ producing coagulation factors. A failing liver causes the patient to have insufficient coagulation factors, which leads to increased chance of bleeding. Coagulation factors are invisible, soluble proteins but they work in conjunction with platelets which are visible, cellular particles. Both systems are needed for adequate control of bleeding in the absence of surgery. When surgery is needed, both systems must be normalized before surgery can be safely performed. Even so, during surgery, one or both systems can fail and will need correction by the health provider.

So, in general, bleeding before, during and after surgery are major challenges. Many patients start to bleed before the operation. If the bleeding site is external and obvious, pressure can be applied to temporarily stop the bleeding. If the red cell concentration (or hemoglobin concentration) is too low, blood transfusion (typically packed red blood cells) will be administered so that the patient can tolerate the anesthesia as well as further blood loss during the surgery.

Due to the nature of surgical interventions, there will be some blood loss from the surgical cut. The surgeon will try to minimize blood loss by not cutting blood vessels if possible. However, in many tissues, the blood will "ooze" out anyway from damaged tissues without the surgeon having to make a surgical cut across the tissue. In those cases, the surgeon will use "cotton swabs" or absorbent material to soak up the blood, so that he can at least have a clear view of the surgical site to continue and finish the surgery. However, any such bleeding due to the physical condition of the patient, the difficulty of the surgical site, or an inadvertent cut by the surgical knife, will require the surgical team to spend time clearing the surgical field, which will prolong the surgical time. A long surgical time can be expensive due to the large number of other highly paid personnel around to help with anesthesia and the surgery.

Some surgeries will have continued blood loss post-operatively even though the surgeon controls bleeding adequately during the operation. Examples include the operation of the knee or hip: blood will continue to be lost from the matrix of the bone, which the surgeon cannot "close with a suture." When it is found that the patient has become thrombocytopenic, platelets will be transfused. If the coagulation system is dysfunctional, specific coagulation factors (or a combination of coagulation factors, such as found in fresh frozen plasma, or cryoprecipitate) will be transfused. Unfortunately, transfusion of blood products often leads to transfusion reactions which can cause additional complications for the patient.

Therefore, it is beneficial to have a product that can control bleeding before, during and after a surgical operation so that (a) the patient can recover faster, and/or (b) the health provider spends less time clearing the surgical field and can complete the surgery faster. The meaning of "control" in this application means not only the reduction in the amount of blood loss, but also an absence of blood in the surgical field, or having only a small amount of blood there so that the surgeon is not stressed out and the time of surgery can be reduced compared to similar cases where the patient is not administered with the present invention. The patient will benefit from a faster discharge from the hospital and suffers less from the complications of transfusions.

The following summary of methods of the present invention are illustrated:

(1) It has been found according to the present invention that a suspension of albumin nanospheres can be produced by a new method, such as but not limited, by (a) starting with ingredient solutions all at cold temperatures (defined as between 2° C. and 6° C.) and (b) having them mixed in the correct order and volume ratios, also at cold temperature, (c) warming the suspension to room temperature (defined as between 18° C. to 25° C.). The ingredient solutions are an albumin solution, a low-concentration glutaraldehyde solution, and an alcohol solution which contains glutaraldehyde at a concentration capable of completely crosslinking the molecules making up the nanosphere so that the nanosphere does not redsissolve upon further processing.

(2) It has been found according to the present invention that a suspension of fibrinogen-coated albumin nanospheres can be produced using the method (1) above, by the addition of a fibrinogen solution after the nanospheres have been stabilized against resolubilization in room temperature.

(3) It has been found according to the present invention that the method (1) and method (2) allows adequate time for the addition and mixing of large quantities of ingredient solutions without the problem of poor mixing conditions leading to the formation of clumps, aggregates or spheres larger than desired. The quantity that can be produced easily is enough to produce 4000 bottles of final products a day, each with 100 ml of spheres at 8 mg per ml of final product.)

(4) It has been found according to the present invention that the method (1) and method (2) can be modified so that only the albumin solution is first equilibrated to room temperature but that the low-concentration glutaraldehyde solution and the alcohol solution (containing a higher concentration of glutaraldehyde) are initially equilibrated to cold temperature. The addition and mixing of the solutions will be done in cold temperature so that the nanospheres (which have not been stabilized) would be formed in cold temperature. Subsequent warming of the turbid suspension will lead to stabilization of the spheres.

(5) It has been found according to the present invention that the product, i.e. the population of spheres in the suspension formed under method (1) will have a size distribution more homogenous than the population of spheres formed when the ingredient solutions were all added and mixed and incubated at room temperature, or a higher temperature.

(6) It has been found by the present invention that the product-by-the-method of (a) combination of method (1) and method (2), and (b) combination of method (4) and method (2), i.e. fibrinogen-coated nanospheres produced whether the starting temperature of the albumin solution is at cold temperature or at room temperature; the spheres are effective in reducing bleeding time and reducing the volume of blood loss during surgery, including a surgical cut to the liver in a live animal.

(7) It has been found by the present invention that non-thrombocytopenic (normal platelet count) surgical patients who will undergo surgeries involving soft tissues and organs that tend to bleed can be treated with fibrinogen-coated albumin nanospheres intravenously prior to the surgery so that they will bleed less.

(8) It is expected from the present invention that non-thrombocytopenic patients having surgeries involving bone can benefit from the administration of the present invention, including the intravenous administration of fibrinogen-coated albumin nanospheres pre-operatively so that they bleed less intraoperatively and post-operatively. Bone surgery would include the repair of bone fractures, or the replacement of natural joints with artificial joints (such as the knee joint, or hip joint.) Due to the fact that a suction cup is often attached to the drain from the surgical site, the amount of blood loss can accurately be measured.

(9) It has been found by the present invention that the control of bleeding produced by the present invention includes not only reduction in the bleeding time, or the reduction in the volume of blood loss during surgery, but that the surgical field is cleaner and less flooded by blood so that the surgeon is less stressed and can complete the surgery faster.

(10) It has been found by the present invention that the suspension of fibrinogen-coated albumin nanospheres made with the present invention can be further processed to increase its shelf-life in room temperature, i.e. by adding an excipient to the suspension and then lyophilizating the suspension into a solid. The excipient can comprise of any number compounds with negative charges including and not limited to glycine at a pH greater than its pI (for glycine with pI of 5.9, the pH of the suspension must be above pH 5.9).

(11) It has been found by the present invention that the lyophilized solid comprising of dried fibrinogen-coated albumin nanospheres, sorbitol and glycine can be reconstituted with water and will result in a suspension of similar-sized nanospheres without the presence of aggregates.

(12) It has been found by the presence invention from preliminary stability tests that the lyophilized solid comprising of dried fibrinogen-coated albumin nanospheres, sorbitol and glycine can probably have a self-life of storage in room temperature for more than ten years.

The present invention is a new method of producing a suspension of albumin nanospheres in a large scale and yet maintaining a narrow distribution of sizes of the nanospheres. The new method utilizes the effect of cold temperature during the formation of the particles. The nanospheres may be subsequently coated with fibrinogen. Fibrinogen-coated nanospheres produced by this method are effective in controlling bleeding in non-thrombocytopenic subjects during surgeries, including the reduction in bleeding time and the volume of blood loss caused by a laceration in the liver. The suspension can be lyophilized resulting in a long shelf-life of storage in room temperature.

Experiments

Experiment One: Production of Large Quantities of Nanospheres in Cold Temperature Purpose:

To evaluate the effect of cold temperature on the formation of spheres and the size distribution of the spheres in the suspension.

It has been discovered in some pilot experiments that the size of the spheres formed is affected by the size of the container, i.e. the larger the container, the larger the spheres. This suggests that temperature may be a factor that needs to be controlled. It is known that the mixing of alcohol with water generates heat (exothermic reaction.) It stands to reason that large containers are only used when large volumes of solutions are mixed for the purpose of producing large batches of spheres. However, large containers are harder to dissipate heat; in contrast to small volumes mixed in small tubes, which can easily dissipate heat upon shaking of the tube in room temperature to mix the ingredients. In some pilot experiments several of the ingredient solutions needed to make albumin spheres were first equilibrated to a temperature lower than room temperature (defined here as 18° C. to 25° C.), but the albumin solution was always maintained at room temperature before the other solutions were added and well-mixed to produce spheres. This experiment evaluates the effect of cold temperature, particularly when the albumin solution may also be equilibrated first to cold temperature (defined as 2° C. to 6° C.) It is not apparent nor obvious before the data were obtained that cooling the albumin solution to a cold temperature would make any major difference in the production of spheres or the size distribution of the spheres.

Materials and Methods:

Human serum albumin (25%) can be purchased from any commercial supplier and was used directly without dialysis or the addition of any surfactant or detergents; it was diluted with deionized water to the "initial albumin concentration." The initial albumin concentration is defined as the concentration of albumin in a solution before the addition of any of the other solutions designed to form spheres by the desolubilization of dissolved albumin molecules from the dissolved state. In most of the prior art disclosed by Yen, all the ingredient solutions (including the albumin solution, glutaraldehyde solution, alcohol solution) were mixed in room temperature, and there was no teaching on the importance of temperature control, particularly when large volumes were to be produced.

Albumin solutions were first prepared by dilution of 25% albumin solution with water to 6% (w/v). Glutaraldehyde solution was diluted from a 10% solution with water to 0.15 mg per ml; at this concentration, the glutaraldehyde was not concentrated enough to crosslink the spheres completely (the spheres were to be formed in the next step where alcohol was added) or to the extent that the spheres could resist solubilization when the alcohol concentration in the suspension was reduced. However, this step of first mixing the albumin solution with the low concentration of glutaraldehyde solution would render the size of the spheres more homogenous than if this step was not used.

Alcohol solution was ethyl alcohol (75% diluted in water) containing also a crosslinking concentration of glutaraldehye at 0.5 mg per ml. The alcohol solution was typically added in two portions: addition of all the alcohol in one step would often cause random precipitation of the albumin molecules into a useless paste (useless with respect to the formation of spheres.) Dividing the total volume of alcohol solution into two portions allows the well mixing of the albumin-glutaraldehyde mixture with the first alcohol portion first. The result of mixing the albumin solution-plus glutaraldehyde-plus first portion of alcohol is a still-clear, slightly-yellow solution, indicating that spheres have not yet formed.

The presence of this volume of the first portion of alcohol will have the effect of reducing the "initial concentration of albumin" to a much lower concentration, depending on the actual volume of each ingredient solution added so far. The spheres will form only upon the addition of the second portion of the alcohol solution. The property of the spheres will be decided mainly by the amount (the volume and the concentration of alcohol) of the second portion of alcohol added, against a "reduced" albumin concentration (reduced as compared to the "initial albumin concentration", because of the volume of glutaraldehyde solution and the first portion of alcohol solution already added.) In this experiment, the effect of temperature will be demonstrated.

Four 15-ml polypropylene tubes were used to prepare the spheres in four conditions. The initial temperatures (i.e. before mixing) of the ingredient solutions were achieved by equilibration in a water bath or inside an ice-water bucket. The temperature of the ingredient solutions were measured directly with a digital thermometer. The following Table 1 outlines the temperatures of the environment during the first 2 hours after both portions of the alcohol solutions have been added, followed by the next 2 hours, for the purpose of assessing temperature effect on the formation of the spheres.

TABLE 1

| Tube | Initial Temperature of albumin solution | Temperature of environment after formation of spheres, first two hours | Temperature of environment for the next two hours ($3^{rd}$ and $4^{th}$ hour) |
|---|---|---|---|
| W | Room temp | Room temp | Room temp |
| X | Room temp | Cold temp | Room temp |
| Y | Cold temp | Room temp | Room temp |
| Z | Cold temp | Cold temp | Room temp |

Specifically, the initial temperature of the 6% albumin solution in tube Y and Z were 2.9° C. and 2.5° C., respectively. The temperature of the "room temp" water bath was 23.3° C. (which was also the temperature of the albumin solutions in tube W and X.) The glutaraldehye solution was 4.0° C. (before adding to all 4 tubes). The initial temperature of the alcohol solution (before adding to all of the solutions in the 4 tubes, always in two aliquots) was 5.3° C.

The volume of the albumin solution was 2 ml inside the tube. At time zero, one ml of the glutaraldehye solution (at 4° C.) was added to the tube and the mixture was completely mixed by capping the tube and inverting the tube 3 times. At time equal to 60 seconds (plus or minus 5 seconds) the first aliquot of alcohol (at 5.3° C.) was added (2.6 ml) and the contents were immediately and thoroughly mixed. At time equal to 150 seconds (plus or minus 5 seconds), the second aliquot of alcohol (at 5.3° C.) was added (4.2 ml) at which time the previously-clear solution turned into a turbid suspension, indicating the formation of spheres. During the time from zero to 150 seconds, for tube W and X, the tubes were placed into the water bath set at room temperature; for tube Y and Z, the tubes were placed back to the ice-water bucket to maintain cold temperature during this short interval. Thereafter, Tube W and Y were placed in the room temperature water bath and tube X and Z were placed in the cold temperature environment.

At two hours after the appearance of turbidity, a sample of the turbid suspension (100 microliter) was removed from each of the tubes and diluted with 900 microliter of water in separate tubes labeled W2, X2, Y2, and Z2. In all previous experiments (since Yen's first disclosure of the manufacture of albumin spheres) the spheres would have been stabilized by this time, by the crosslinking action of glutaraldehye and the spheres would not be re-solubilized; and the diluted suspension would remain turbid. However, this is not entirely the case as observed in the Result section to follow.

Results:

The following Table 2 summarizes the results obtained in the four tubes under four conditions of manufacture of the spheres.

TABLE 2

| Tube | Temperature of suspension when turbidity first appeared, ° C. | Spheres stabilized after two hours in the presence of high concentrations of glutaraldehyde? | Spheres stabilized against resolubilization during $3^{rd}$ and $4^{th}$ hour post-synthesis? |
|---|---|---|---|
| W | 21.2 | Yes | Yes |
| X | 21.7 | No | Yes |
| Y | 17.8 | Yes | Yes |
| Z | 17.1 | No | Yes |

The temperature of the suspension when turbidity first appeared was measured. It is not surprising that in the case of tube W and tube X, on mixing two volumes of albumin at room temperature with a total of 7.8 volumes of cold solutions (one volume of glutaraldehye, 6.8 volumes of alcohol solution) that the resulting suspension is between 21.2° C. and 21.7° C., rather than at a temperature closer to the "cold temperature." This is due to the heat generated on mixing an alcohol solution with an aqueous solution.

This was further validated by the temperature of the suspension when spheres were formed, by the temperatures in tube Y and Z. All of the solutions including albumin were initially at cold temperature, and yet the mixture became 17.8° C. and 17.1° C., respectively, from the exothermic reaction upon addition of the alcohol solutions to the albumin-glutaraldehyde-solution mixture.

Although spheres were formed in all four tubes, as evidenced by the equally turbid appearance of the suspensions, the spheres in tube X and Z were not stable. Upon dilution with water (reducing the concentration of alcohol by the dilution) after 2 hours of incubation in the cold temperature, the spheres still redissolved and the turbidity disappeared immediately. This had never been observed before and was never reported before. The result was totally unexpected.

However, on transfer of tube X and Z to room temperature for the next two hours (the 3rd and 4th hour) the spheres became stabilized by the action of glutaraldehye. Examination of the spheres in the suspension revealed no aggregations, and the size distribution in tube X and Z appeared to be narrower than the size distribution of the spheres in tube W and Y, i.e. the spheres were more homogenous in size when stabilized slowly during the 3rd and 4th hours in room temperature.

A sample of the suspension was taken after the second hour and after the fourth hour from each of the tubes. The sample was further diluted with water (10 fold dilution) to allow resolubilization if the spheres were not stable, and then the amount of spheres in the diluted sample was assayed.

The following Table 3 showed the yield of spheres in the reaction at the 120 minute and 240 minute after the formation of spheres in the suspension.

TABLE 3

| Tube | Temperature for first 2 hours after appearance of turbidity | Mass of spheres as percent of Total Protein concentration (Yield of spheres, mg/mg) in sample taken at 120 min post-synthesis of spheres | Temperature for second 2 hours ($3^{rd}$ and $4^{th}$ hour) after appearance of turbidity | Yield of spheres in sample taken after the $4^{th}$ hour, mg of sphere per mg of total protein, in % |
|---|---|---|---|---|
| W | Room temp | 89 | Room temp | 86 |
| X | Cold temp | 5 | Room temp | 89 |
| Y | Room temp | 89 | Room temp | 89 |
| Z | Cold temp | 3 | Room temp | 88 |

The data showed the importance of having room temperature for the stabilization of the spheres, regardless of the temperature at which they are formed, and regardless of the initial temperature of the ingredient solutions.

The spheres in tube W and Y achieved stabilization within the two hours after formation of the spheres, resulting in high yields (89% of all albumin molecules formed spheres, with the remaining 11% remaining as soluble proteins.) Further incubation in room temperature for two more hours did not substantially increase the yield of the reaction. The drop of the yield in Tube W from 89% to 86% was probably an assay technical inaccuracy.

The spheres in Tube X and Z did not achieve stabilization during the two hours in the cold temperature even though the same concentration of glutaraldehye (sufficient to achieve stabilization) as in tube W and Y were present. It should be noted that in The present invention, a high concentration of the glutaraldehyde molecules were present in the cold suspension where the spheres were already formed. This is in strong contrast to the teachings of the prior art, where it was contemplated that glutaraldehyde could be added (by the "Post-link" method) to a suspension of totally non-crossed linked spheres, where there was no glutaraldehyde present at all, to achieve stabilization of the spheres after their formation.

As evidence that the spheres in the cold temperature did not achieve stabilization, it was observed that dilution with water would cause the majority of spheres to redissolve, leaving only 3 to 5% of the initial mass of albumin molecules in the form as spheres, after the dilution with water. However, the unstable spheres did not aggregate during this time of incubation in the cold temperature or during warming to room temperature, as shown by microscopic examination after the 4th hour. During the 3rd and the 4th hour at room temperature, the spheres became stabilized and the yield became comparable to those in tube W and Y.
Comment:

The discovery of delayed stabilization of spheres, i.e. by forming spheres first in cold temperature followed by slow warming to room temperature, will have great impact on the production of useful suspensions of spheres in a large scale.

In almost all of Yen's prior experiments, the initial temperature of the albumin solution was almost always at room temperature because the addition and mixing of the ingredient solutions could not be done easily in any other temperature. The containers were not heat-insulated or cold-insulated. It was hard enough to equilibrate the alcohol solution alone, to one specific temperature between zero and 18° C. The temperature of the suspension when turbidity first appeared also varied according to the shape and size of the container in which the ingredient solutions were mixed: due to the difficulty in heat dissipation in large containers.

The action of glutaraldehye was fast. Using the conventional method (prior art by Yen) typically within 10 minutes of the addition of the alcohol solution (containing 0.5 mg of glutaraldehyde per ml of alcohol solution) the albumin molecules became linked together and some spheres would be stable enough to resist resolubilization. The spheres might become smaller in volume due to partial solubilization before the 10 minute time point, but they did not all redissolve upon reduction of the alcohol concentration. Therefore, the addition of the entire volume of the second portion of the alcohol solution must be completed within 60 seconds. However, in large scale productions, it takes time to complete the last step which is the complete emptying of the second portion of the alcohol solution into the "reaction container" (which now contains the mixture of the albumin solution, the glutaraldehye solution and the first aliquot of the alcohol solution.). From the start of pouring, to the last drop of the second aliquot of alcohol going into the reaction container, it might need more than 60 seconds before the entire volume could be poured into the mix in the reaction container. In addition, the entire volume (sum of the volumes of the albumin solution, the glutaraldehyde solution and the two aliquots of alcohol solution) must be thoroughly mixed within seconds. This poses a challenge because in a large scale production, it often requires more than 60 seconds to completely pour the second aliquot of alcohol solution into the reaction container. Improper mixing or delayed mixing of the solution would result in areas where alcohol was either in excess or was insufficient, thus resulting in aggregates of spheres, or low yield.

This experiment showed that when all the ingredient solutions were initially equilibrated to cold temperature, and then mixed in cold temperature, although spheres were formed, they did not aggregate into clumps or change in size, as long as the suspension was maintained in cold temperature. This suggests that in a large scale production the entire addition of ingredient solutions and their mixing could be done in a cold room. And then the reaction container containing the to-be-stabilized spheres could be brought to room temperature to achieve stabilization of the spheres without the formation of unwanted clumps or aggregates.

It is not clear from this experiment whether the site of linkage on the albumin spheres achieved (even to a limited extent) in the cold temperature were the same as those formed entirely in room temperature. While the reaction of glutaraldehyde molecules with amino acids were predictable, there are different site on the albumin molecule where glutaraldehyde molecules might react differently under different temperatures. Therefore the products (spheres) formed in the cold (and then warmed to room temperature) may not be the same at the molecular level, or sphere level, as the products formed entirely at or above room temperature.

The formation of spheres at room temperature might as visualized as follows: within the first 60 seconds, on mixing of the low-concentration glutaraldehye solution with the albumin solution, some cross linking of albumin molecules would have occurred. However, the spheres were not formed until the second portion of alcohol (containing additional concentrations of glutaraldehye) was added. Thereafter, the spheres would begin to be stabilized against resolubilization within about 10 minutes.

In contrast, the formation of spheres in The present invention (initially at cold temperature, and then at room temperature) would be different in the following sense: the presence of glutaraldehyde molecules (whether supplied by the low-concentration glutaraldehye solution or from the alcohol solution) did not result in any substantial crosslinkage of the albumin molecules during the time period when the spheres were incubated in the cold temperature. However, there was no question that the spheres had been formed after the addition of the second aliquot of the alcohol solution because the suspension was turbid and blurry images could be seen under the microscopy. It was only when the suspension was transferred to room temperature that the stabilization occurs. This provides a window of much longer than the 60 seconds needed for the mixing of the second portion of alcohol than when the production was done in room temperature according to the prior art. In other words, large volumes of the ingredient solutions could be mixed together in the cold temperature without any problem even though the time needed for the mixing of these solutions would take more than 60 seconds (for example, in this case the window was 2 hours in the cold temperature.) Only after the spheres were formed, during which time they would not form aggregates or became larger or smaller, then would the reaction mixture be brought slowly to room temperature.

Examination of the sphere sizes under the microscope showed that the spheres were less than one micron in diameter in tube W and Y but there are some (probably about 1%) that are larger than one micron in diameter. The spheres in tube X and Z were also less than one micron but there were no spheres observed that were larger than one micron in diameter. Therefore, the size distribution of spheres formed initially in the cold temperature followed by incubation in room temperature appeared to be more homogenous in size.

Experiment Two: Efficacy of Fibrinogen-Coated Albumin Nanospheres (FAS) in Controlling Bleeding During a Surgical Procedure.

Purpose:

To measure the bleeding time and bleeding volume in FAS-treated versus saline-treated control rats undergoing liver surgery.

Liver laceration was a common result of car accidents before seat belts were widely used. Upon impact, the abdomen offers little protection for the soft liver tissues which could suffer from a blunt trauma or a laceration if there were sharp or hard objects in the front seat. If FAS could be quickly administered for example in the ambulance, the patient might benefit from a less severe case of internal bleeding.

In Yen's prior art disclosures, the use of FAS was directed toward thrombocytopenic subjects. It was difficult to demonstrate efficacy in the non-thrombocytopenic subject because bleeding time was already "normal." In this experiment the goal was to find out if FAS was effective in controlling bleeding in a surgical setting, even in non-thrombocytopenic subjects (i.e. normal platelet counts.)

In Yen's prior art disclosures, the use of FAS was anticipated in the surgical setting. But the anticipated use was on patients who were expected to become thrombocytopenic due to major blood loss. In some cases of major blood loss, the surgical team only transfuses red cells without transfusing platelets, leading to a condition called "dilutional thrombocytopenia." The present experiment is different from these previously described conditions because at the time of evaluation, the patient had normal values in coagulation factors and platelet count and had no expectation of major blood loss. The hemostatic function of the subject was normal at the time of evaluation of the efficacy of FAS in this animal model.

Materials and Methods:

The suspension containing fibrinogen-coated nanospheres was prepared using the conditions of tube W, except larger volumes of ingredient solutions were used to result in 3 liters of blank albumin nanosphere suspension. At the 4th hour, one liter of fibrinogen solution (at 1.8 mg fibrinogen dissolved in a solution containing 1 mg of sodium tetradecyl sulfate per ml) was added at room temperature to coat the spheres. Thereafter, the alcohol was reduced by a method (to be disclosed in another patent application) under aseptic conditions and other excipients were added. The final suspension contained spheres at 8 mg per ml of suspension, ethanol not more than 5%, sorbitol not more than 5% and sodium caprylate at 13.3 mg per gram of protein (whether in the form of spheres or in the form of soluble protein.) The suspension was dispensed to 100 ml bottles. After the bottles were capped and sealed, the contents were subject to a terminal pasteurization at 60° C. for 10 hours.

The dose to the rats was 16 mg per kg administered intravenously. For control, normal saline at 2 ml per kg was administered, also intravenously.

Naïve Sprague Dawley male rats, 6-8 weeks old were used. The study design was as follows:

1. Ten (10) rats received from tail vein injection a dose of FAS at 16 mg per kg weight of animal (product contained 8 mg product per ml; i.e. 2 ml per kg wt of rat.) Wait 4 hours.
2. Ten (10) rats received from tail vein injection a dose of 2 ml normal saline per kg weight of the animal. Wait 4 hours.
3. After general anesthesia by isoflurane, aseptic surgical procedures were applied to generate one single laceration (incision of central lobe) of approximately 5 mm in length and 2 mm in depth. Blood was allowed to free-flow. No pressure was applied to the cut.
4. The time from surgical cut to "spontaneous cessation of bleeding" without interference was noted. This time measured in seconds is called "bleeding time."

5. The amount of blood lost was captured by pre-weighed cotton and measured.
6. The surgical procedure and bleeding after the laceration were videotaped for all the animals.

Results:

The following Table 4 shows the bleeding time and bleeding volume after the cut in the rat liver.

TABLE 4

| Group | Animal ID | Amount of bleeding (mg) | Bleeding time of laceration(s) | Re-bleed |
|---|---|---|---|---|
| Test product | 4827 | 314 | 120 | No |
| | 4830 | 381.4 | 120 | No |
| | 4834 | 418.2 | 120 | No |
| | 4837 | 235.3 | 120 | No |
| | 4840 | 351.7 | 60 | No |
| | 4841 | 319 | 60 | No |
| | 4844 | 303.1 | 60 | No |
| | 4845 | 287 | 60 | No |
| | 4846 | 274.1 | 60 | No |
| | 4848 | 336.5 | 60 | No |
| | MEAN | 322.03 | 84 | — |
| | SD | 53.06 | 30.98 | — |
| Saline | 4826 | 540.6 | 180 | No |
| | 4828 | 607.5 | 240 | No |
| | 4829 | 764.6 | 60 | No |
| | 4832 | 880.8 | 60 | No |
| | 4833 | 862.9 | 120 | No |
| | 4836 | 782.4 | 120 | No |
| | 4839 | 582 | 60 | No |
| | 4842 | 683.2 | 60 | No |
| | 4843 | 692.6 | 120 | No |
| | 4847 | 678.2 | 60 | No |
| | MEAN | 707.48 | 108 | — |
| | SD | 114.66 | 61.97 | — |

1.1 Bleeding Time of Laceration

Figure 1:
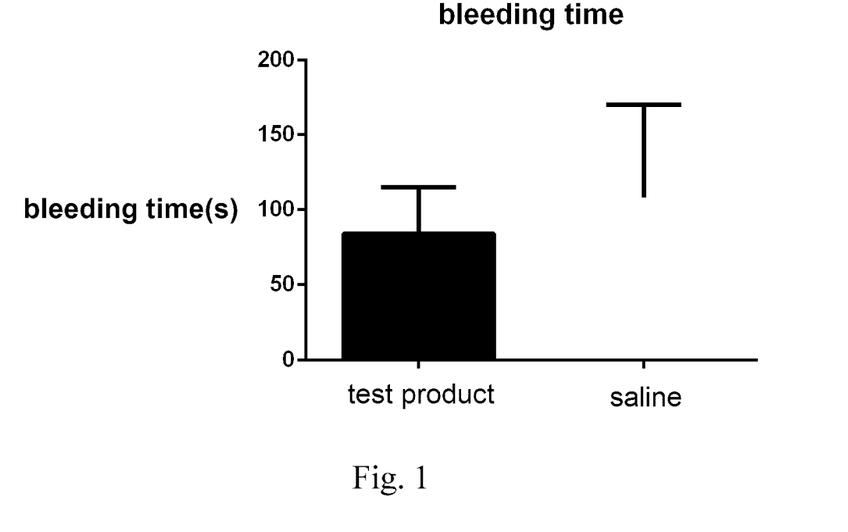
FIG. 1 is a graphical view of the bleeding time comparison between a test group using the present invention and a control saline group.

The averaged bleeding was about 24 seconds quicker in the test (FAS) group, as compared to that of the saline injected control group, as illustrated in FIG. 1. Because of the large variation within the saline injected control group, about 95%, there was no statistical significance detected between the two groups on this parameter. A larger sample size should correct this problem.

1.2 Amount of Blood Lost

Figure 2:
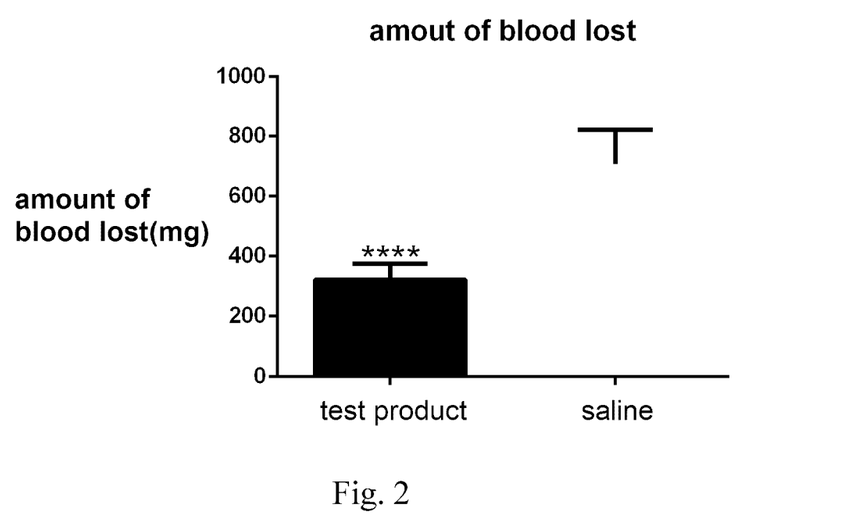
FIG. 2 is a graphical view of the blood lost comparison between a test group using the present invention and a control saline group.

The average amount of blood lost was significantly lower in the test group, as compared to that of the saline injected control group, as illustrated in FIG. 2. The weight of blood loss in the FAS-treated group was 45.5% that of the blood loss in the saline-treated control group.

Conclusion

The test compound injected 4 hours prior to the laceration effectively and significantly reduced the amount of blood loss. The bleeding time was also reduced by the test compound although the variation in the saline injected control group prevented the statistical significance.

Comments:

Although a dose of 16 mg spheres per kg was used here, we believe that the standard dose of 8 mg spheres per kg weight of the animal would be equally effective.

This method is sensitive enough to provide evidence of stability after storage of the suspension over one or two years under a variety of conditions, including elevated temperature, cold temperature or room temperature. During long term storage of the product, one would expect some detachment of fibrinogen from the spheres with time, regardless of how small an amount. In order to know whether such minute degree of decrease in fibrinogen content (defined as mg of fibrinogen attached per mg sphere) would be clinically significant, the product after the storage period or condition needs to be evaluated in a bleeding model. This liver laceration model is easy to set up because there is no need to generate the thrombocytopenic condition. The difference in the bleeding volume is highly statistically significant even with 10 rats per group. Therefore, the bleeding volume obtained after the storage period would be a good indication of efficacy after that period of storage, especially if both doses (8 mg per kg and 16 mg per kg) were evaluated at every evaluation time point.

Although this experiment used spheres generated under the condition of tube W followed by coating with fibrinogen, we expect the spheres generated under the conditions of tube X, Y and Z, followed by coating with fibrinogen in room temperature, would be equally effective.

We expect good control of bleeding under conditions where the entire lobe was removed or resected (as in a living donor having his right liver lobe removed.)

We also expect good control of bleeding by the present invention in cases of liver cancer which had distorted the normal anatomy of the liver, making it more likely to bleed than when surgery was done in a normal liver.

We allowed 4 hours for circulation of FAS from the injection site (any vein) to the liver. It may be possible that fewer hours are needed. Due to the small size of the particles, we expect the FAS to circulate within the circulatory system near the endothelium, rather than in the center of blood vessels. As such, the bulk of the FAS would not easily reach the liver (like other soluble drugs which would be carried by the bulk of the blood constantly flowing to the liver to be metabolized.) It may even be possible that FAS is effective when administered after the liver was lacerated or cut.

The surgical cut was observed for at least 15 minutes to see if the site bled again. The data showed that there was no re-bleeding, indicating that the clot formed in the presence of FAS treatment is not weaker than the clot formed without FAS.

Experiment Three: Lyophilization of the Nanosphere Suspension and Reconstitution of the Lyophilized Solid to Result in a Functional Suspension Purpose:

To find conditions of lyophilization where the nanospheres will not aggregate and where the nanospheres in the solid will have long shelf-life during storage in room temperature Rationale:

Known disclosures, such as Zee ("A Novel Device for Promoting Healing From Surgical and Medical Treatment, Its Use and Method of Production", applied for in China 1995; "A Method for Promoting Healing From Surgical and Medical Treatment, Its Use and Method of Production", applied for in China 1995) has mentioned with little detail the manufacture of a lyophilized product comprising of fibrinogen-coated microspheres. However, it is now known that the suspension at the time of the start of lyophilization included a high concentration of excipients, including: 2.8% glycine, 2.4% lactose, 2.4% maltose (a total of 7.6%, w/v) but no sorbitol. The spheres in that disclosure have a median size larger than one micron which will settle easily during storage.

In the Yen prior art entitled "Mass Production of Ready-to-use Suspensions of Fibrinogen-coated Albumin Spheres for the Treatment of Thrombocytopenic Patients" (US patent application, publication number 20140030347, Jan. 30, 2014) gave a good description of the disadvantages of the Zee product describe a specific type of albumin spheres suitable for use as artificial platelets. However, the method of production includes the addition of a surfactant, e.g. sodium tetradecyl sulphate or Tween-80 to ensure that the spheres do not form aggregates greater than 7 micron in diameter which can clog blood vessels. Zee also disclosed that the product made by his method requires lyophilization for long term storage. Although Zee claimed that the "average" size of the product made by his method is less than one micron, it is obvious that the product contains some large spheres which are larger than one micron. Spheres larger than one micron cannot remain suspended for long by the Brownian movement of water molecules. Regardless of the percentage occupied by these large spheres, these larger-than-one micron spheres will quickly settle to the bottom of the container. It is not possible to separate such sediments back into single spheres by merely shaking the container. The presence of clumps in the settled layers can cause obstruction of blood vessels if administered intravenously to a patient. As a result, the product of Zee must be lyophilized soon after their synthesis during the entire manufacturing process and the dried powder needs to be converted back into a suspension by reconstitution with a fluid at a time immediately before administration to a patient. The spheres within a reconstituted suspension manufactured by Zee will sediment into a bottom layer which is visible by the unaided eye within 8 hours."

Here we started the lyophilization process with a suspension that contains at least 3 to 5% of sorbitol, with the addition of a range of low concentrations of a negative compound comprising and not limited to glycine. The purpose is not to solve the problem of spheres settling to the bottom of the container forming "cakes" that cannot and must not be administered to patients intravenously. The purpose here is merely to provide long shelf lives. The spheres here are nanometer in size and do not easily settle to the bottom of the container upon storage, with or without lyophilization, before and after reconstitution of the lyophilized product.

Amino-acids by definition have at least an amino terminal which is positively charged and an acid terminal which is negatively charged. The pH of a solution at which the overall negative charge is the same as the overall positive charge (net zero charge) is called pI, at which pH the amino acid will not migrate in an electric field (because it has in this condition a net zero charge.) The pI of glycine is 5.9. In a buffered solution higher than pH 5.9 the net charge on glycine molecules will be negative. The natural overall pH of a human serum albumin solution (e.g. 25%) is about 6.9±0.5. It was found that the suspension of fibrinogen-coated albumin nanospheres also has a natural (unbuffered by other buffers) pH of about 6.9. Therefore, we know that the overall charge of glycine solutions will be negative in a suspension of albumin spheres, which will help the negative charges on the surface of the spheres to bounce against (repel) each other rather than stick together (attract each other to form aggregates.)

Materials and Methods:

Experiment One describes four methods using solutions starting at different temperatures; but after incubation at room temperature nanometer-sized albumin spheres are formed without the presence of aggregates. All four products from the four methods are evaluated, with these following steps to prepare them for lyophilization. All four preparations produce similar results.

The steps are: after a stable suspension of nanospheres were obtained, excessive alcohol was removed by dialysis against water until the alcohol content was less than 3% (v/v). Thereafter, sorbitol (USP grade) was added to a final concentration of 3% to 5% to achieve osmolarity of the suspension of at least 300 mOsm. This will be called the "sorbitol-containing suspension." After this step, the suspension can be filled into a sterile medical-grade vial, capped and subject to "terminal pasteurization" (heated at 60° C., for 10 hours.) This will be the "ready-to-use" suspension, which will have 8 mg spheres per ml of suspension.

It was found, however, with or without the step of "terminal pasteurization" the suspension containing sorbitol can be processed further with the step of lyophilization as follows:

1. To 6 bottles each containing 100 ml of the sorbitol-containing suspension, either 5 ml of water (control preparation) or 5 ml of a glycine solution is added to result in sorbitol-containing suspensions also containing zero, 50 mg, 100 mg, 200 mg, 300 mg, 500 mg of glycine per bottle.
2. The suspensions are lyophilized using a commercial lyophilizer under the following conditions: (a) freezing time 4 hours, down to −40° F., and then reheated (to provide energy for the sublimation of frozen ice) to 160° F. for over 6 hours; (b) repeated with fresh preparations and then: freezing time 2 hours, down to −40° F., and then reheated (to facilitate escape of water) to 160° F. for over 6 hours.

Result:

The resulting product was a solid like a rock (and not a powder form). It had the texture of a hard-candy. To test if the solid can be reconstituted, 100 ml of water was added. It was found that the solid immediately melts and become reconstituted into a turbid suspension within seconds of the addition of the fluid.

It was found that under condition (a) as described above, the control bottle showed large aggregates when the reconstituted suspension was examined under a phase-contrast microscope. However, within the range of glycine added (0.5 mg per ml to 5 mg/ml) all the other preparations (after reconstitution) contain spheres of the same size-range as before lyophilization, and without any aggregates.

It was found that under condition (b) as described above, all the bottles including the control bottle showed no aggregates in the reconstituted suspension, and the suspensions contained spheres of the same size-range as before the step of lyophilization.

Comments:

It has been known that hard-candies can be stored for decades without change in taste or texture and that they have shelf-lives in room temperature easily over ten years. It is expected therefore the present products of lyophilization will have similar long shelf-lives.

The prior arts taught that high concentrations of a combination of glycine and sugars such as lactose and maltose are needed to achieve a powderly product-of-lyophilization. It is a surprise that in the presence of sorbitol, a low concentration of amino-acid such as glycine at 0.5 mg per ml can stabilize the spheres against aggregation during the step of lyophilization. Concentrations below 0.5 mg of glycine per ml of the sphere suspension have not been evaluated, but potentially can still be effective in offering protection of the spheres against aggregation during lyophilization. Concentrations above 5 mg of glycine per ml have also not been evaluated but should be effective.

Although only glycine is used here in this experiment, any number of amino acids that are negatively charged can potentially add to the surface negative charge of the spheres to help them repel each other which will be particularly important during the step of lyophilization.

It is not clear why the reduction of freezing time from 4 hours to 2 hours during the lyophilization cycle produced useful spheres after reconstitution in one case e.g. condition (b); and useless products in another condition, e.g. condition (a). Additional experiments will be needed to resolve the puzzle.

The time needed to completely reconstitute the solids into a useful suspension is only about one minute. The fluid can be any compatible fluid including water, saline or lactated-ringer solution. These commonly used solutions do not cause aggregation of the spheres in the reconstituted suspension.

The lyophilized product has several advantages over the ready-to-use suspension: (a) a longer shelf life; (b) the weight of the product is only the weight of the spheres and sorbitol and glycine, without the water; therefore about 800 mg of spheres, 3 to 5 grams of sorbitol and not more than 500 mg of dried glycine. In contrast the weight of the content of a ready-to-use bottle is more than 100 grams. The lyophilzation can be done in a sterile biaxially-oriented polyethylene terephthalate bag, such as but not limited to Mylar®) and can result in a lot of savings in shipping cost.

Points of the Present Invention

The present invention is a product comprising of a suspension of albumin spheres which were formed initially by the equilibrium between albumin molecules and alcohol molecules in cold temperature, without the formation of stable crosslinkage between neighboring albumin molecules, even when a sufficient concentration of crosslinking agent was present, followed by a period of effective crosslinkage resulting in a suspension of stabilized spheres with a narrow distribution of size, whereafter the administration of said suspension to a patient results in adequate control of bleeding before, during and after surgery.

The present invention is a method of producing a suspension of albumin spheres comprising the steps of (a) cooling the ingredient solutions to a temperature between 2° C. and 6° C., where the ingredient solutions comprise of an albumin solution, a sub-stabilizing concentration of glutaraldehyde solution and an alcohol solution which also contains a stabilizing concentration of glutaraldehyde; (b) mixing the ingredient solutions in a temperature between 2° C. and 6° C. to produce spheres which are not stabilized against resolubilization; (c) maintaining the temperature of the suspension of spheres between 2° C. and 6° C.; (d) warming the suspension of spheres to a temperature between 18° C. to 25° C., whereby the said suspension can be further processed and administered intravenously to a surgical patient to result in adequate control of bleeding before, during and after the surgery.

The present invention anticipates the additional step of adding a fibrinogen solution to coat the spheres with fibrinogen molecules after the spheres had been stabilized in room temperature against resolubilization.

The present invention also anticipates the additional step of lyophilization of the suspension of spheres by the addition of a low concentration of glycine to the about 3% to 5% of sorbitol in the suspension, resulting in a solid which has shelf life of more than ten years.

The present invention is a method of treating a non-thrombocytopenic surgical patient before, during and after the surgical procedure resulting in adequate control of bleeding leading to a smaller volume of blood loss and shorter surgical time.

The present invention is a method of controlling bleeding in a surgical operation where the surgical cut is done in a tissue or organ where sutures cannot be applied effectively to stop bleeding.

What is claimed as being new and desired to be protected by Letters Patent of the United States is as follows:

1. A method of using a suspension of fibrinogen-coated albumin nano-spheres for intravenous administration to a non-thrombocytopenic patient before surgery to control of bleeding by the patient in association with surgery, said method comprising the steps of:
   a) administering intravenously a predetermined amount of an albumin nanoparticle suspension to a non-thrombocytopenic patient, wherein said albumin nanoparticle suspension consisting of fibrinogen-coated albumin nano-spheres that are not stabilized against resolubilization, a glutaraldehyde solution, sorbitol and a negatively charged amino acid; and
   b) controlling of bleeding of the non-thrombocytopenic patient by said albumin spheres, resulting in at least one of reduced volume of blood loss and reduced surgical time.

2. The method according to claim 1, wherein said sorbitol is at a final concentration of 3% to 5% to achieve osmolarity of said suspension of at least 300 mOsm; and said negatively charged amino acid is glycine.

3. The method according to claim 2, wherein said albumin nanoparticle suspension is a lyophilized albumin nanoparticle suspension reconstituted with water prior to step a).

4. The method according to claim 1, wherein said sorbitol and said negatively charged amino acid are configured at concentrations to inhibit said fibrinogen-coated albumin nano-spheres to aggregate into clumps or spheres larger than a predetermined size that would obstruct blood vessels of the patient when administered to the patient.

5. The method according to claim 1, wherein said predetermined amount of said albumin nanoparticle suspension administered to the patient is at a dose selected from the group consisting of 8 mg spheres per kg weight of the patient, and 16 mg spheres per kg weight of the patient, and said suspension is administered to the patient at a temperature between 18° C. and 25° C.

6. A method according to claim 1 further comprising a suspension of fibrinogen coated albumin nanosphere preparation comprising a suspension of albumin spheres formed initially by equilibrium between albumin molecules and alcohol molecules without the formation of stable crosslinkage between neighboring albumin molecules at a temperature between 2° C. and 6° C., followed by a period of effective crosslinkage at a temperature between 18° C. and 25° C. resulting in said suspension of said of albumin spheres that are stabilized with a predetermined distribution of size.

7. A method according to claim 1 further comprising a preparation of suspension of fibrinogen coated albumin nanospheres comprising the steps of:
   (a) cooling an albumin solution, a sub-stabilizing concentration of glutaraldehyde solution and an alcohol solution containing a stabilizing concentration of glutaraldehyde to a temperature between 2° C. and 6° C.;
   (b) mixing said albumin solution, said sub-stabilizing concentration of glutaraldehyde solution and said alcohol solution at a temperature between 2° C. and 6° C. to produce spheres in a suspension which are not stabilized against resolubilization;
   (c) maintaining the temperature of said suspension including said spheres between or at 2° C. and 6° C.; and (d) warming said suspension including said spheres to a temperature between 18° C. and 25° C.

8. The method according to claim 7 includes an additional step of adding a fibrinogen containing solution to said suspension after said step of warming said suspension to coat said spheres with fibrinogen molecules after said spheres had been stabilized against resolubilization.

9. The method according to claim 7 includes an additional step of lyophilization of said suspension by an addition of at least one amino acid and at least one sugar alcohol.

10. The method according to claim 9, wherein said amino acid is a negatively charged amino acid.

11. The method according to claim 10, wherein said amino acid is glycine and said sugar alcohol is sorbitol.

12. The method according to claim 11, wherein said sorbitol is at a concentration between or at 3% to 5% in said suspension.

13. The method according to claim 12, wherein said lyophilization is performed with said suspension in a sterile bag made of biaxially-oriented polyethylene terephthalate.

14. The method according to claim 7 includes an additional step of removing at least a portion of said alcohol solution by dialysis against water until an alcohol content in said suspension is less than 3% (v/v).

15. The method according to claim 14 includes an additional step of adding sorbitol to a final concentration of 3% to 5% to achieve osmolarity of said suspension of at least 300 mOsm.

16. The method according to claim 15 includes an additional step of adding a negatively charged amino acid to said suspension containing said sorbitol.

17. The method according to claim 16, wherein said negatively charged amino acid is glycine.

18. The method according to claim 17 includes an additional step of lyophilization of said suspension comprising the steps of:
   freezing said suspension at a first temperature for a first time period;
   reheating said suspension at a second temperature for a second time period;
   adding additional sorbitol and glycine to said suspension;
   freezing said suspension at a third temperature for a third time period; and
   reheating said suspension at a fourth temperature for a fourth time period.

19. The method according to claim 18, wherein said second temperature and said second time period is sufficient to provide energy for sublimation of frozen ice, and said fourth temperature and said fourth time period is sufficient for water in said suspension to escape.

20. The method according to claim 18, wherein said first temperature is −40° F. and said first time period is 4 hours, said second temperature is 160° F. and said second time period is at least 6 hours, said third temperature is −40° F. and said third time period is 2 hours, and said fourth temperature is 160° F. and said fourth time period is at least 6 hours.

* * * * *